United States Patent [19]

Cucurou et al.

[11] Patent Number: 6,027,874
[45] Date of Patent: Feb. 22, 2000

[54] IMMUNOENZYMATIC CONJUGATE, METHOD FOR ITS PRODUCTIONS, APPLICATIONS THEREOF

[75] Inventors: Christophe Cucurou, St. Cloud; Gilles Cognet, Yerres; Stéphane Gadelle, Bievres; Carine Le Sager, Chatou, all of France

[73] Assignee: Pasteur Sanofi Diagnostics, Marnes La Coquette, France

[21] Appl. No.: 08/714,110

[22] PCT Filed: Jan. 23, 1996

[86] PCT No.: PCT/FR96/00113

§ 371 Date: Nov. 22, 1996

§ 102(e) Date: Nov. 22, 1996

[87] PCT Pub. No.: WO96/23226

PCT Pub. Date: Aug. 1, 1996

[30] Foreign Application Priority Data

Jan. 23, 1995 [FR] France ................................. 95 00735
May 18, 1995 [FR] France ................................. 95 05939

[51] Int. Cl.[7] ....................................... C12Q 1/70
[52] U.S. Cl. ................................ 435/5; 435/7.1; 435/7.9; 435/7.92; 435/968; 435/974; 436/820; 530/387.1; 530/388.3; 530/826

[58] Field of Search ................................. 435/5, 7, 1, 7.9, 435/7.92, 968, 974; 436/820; 530/387.1, 388.3, 826

[56] References Cited

U.S. PATENT DOCUMENTS

| | | | |
|---|---|---|---|
| 4,256,833 | 3/1981 | Ali et al. | 435/7 |
| 4,693,969 | 9/1987 | Saxena et al. | 434/7 |
| 5,191,066 | 3/1993 | Bieniarz et al. | 530/391.1 |

FOREIGN PATENT DOCUMENTS

| | | |
|---|---|---|
| 0175560A3 | 9/1984 | European Pat. Off. . |
| 0209155A1 | 7/1986 | European Pat. Off. . |
| 0430510A3 | 11/1990 | European Pat. Off. . |
| 4237479A1 | 6/1992 | Germany . |

*Primary Examiner*—Jeffrey Stucker
*Attorney, Agent, or Firm*—Jacobson, Price, Holman & Stern, PLLC

[57] ABSTRACT

Immunoenzymatic conjugate consisting of glycosylated labelling enzymes in copolymer form and substances having immunological activity.

Method for the production of the conjugates according to the invention and use of the said conjugates in diagnostic kits.

29 Claims, No Drawings

IMMUNOENZYMATIC CONJUGATE, METHOD FOR ITS PRODUCTIONS, APPLICATIONS THEREOF

The present invention relates to an immunoenzymatic conjugate consisting of substance(s) having immunological activity and glycosylated labelling enzyme(s) in copolymer form. The invention also relates to the method for the production of the conjugate according to the invention and to the use of the said conjugate for diagnosis.

Various conjugates and methods for the production of immunoenzymatic conjugates are known from the prior art. These immunoenzymatic conjugates generally consist of a substance having immunological activity and a labelling enzyme which may be glycosylated. The methods for the production of these conjugates are varied, and there are, in particular, methods such as those employing periodate coupling techniques, which have given rise to more sophisticated methods employing homo- or heterobifunctional agents. The object of these methods is to improve the coupling of the enzyme to the substance having immunological activity in order to obtain conjugates which enable the specificity and/or sensitivity of the diagnostic results to be increased.

The coupling method of Nakane (The Journal of Histochemistry and Cytochemistry, vol.22, No.12, pp.1084–1091, 1974) describes, after oxidation of the carbohydrates of the enzyme with periodate, the direct coupling of the protein via its free amine groups. Patent EP 209,155 describes a method enabling the immunological reagent to be coupled to the protein portion of the enzyme. According to this method, the enzyme is subjected to an oxidation using periodic acid before or after its coupling with the immunological reagent. The oxidation product thereby obtained is then reduced with sodium borohydride. As regards the coupling, this is carried out using traditional reagents, such as glutaraldehyde, or succinimide derivatives. This method does not employ any copolymerization step. The conjugates originating from this method enable false positive results arising from so-called "problem" sera to be eliminated.

Similarly, Patent Application EP 601,318 describes a method of coupling the immunological reagent to the enzyme via a diamine followed by a heterobifunctional reagent (succinimide derivative), the diamine having reacted beforehand with the oxidized portion of the carbohydrate of the enzyme. A non-copolymerized conjugate, in which the enzyme-immunological reagent link occurs on the carbohydrate portion of the enzyme. In effect, according to this coupling method, the carbohydrate groups borne by the protein are used to graft the protein to the antibody directly.

More recently, Patent Application EP 560,912 and U.S. Pat. No. 5,191,066 describes a method for the production of immunoconjugates (antibody-alkaline phosphatase) using the carbohydrate portion of the proteins, thereby enabling the immunological recognition site of the antibody to be preserved.

Some methods enabling immunoenzymatic conjugates to be obtained in the form of copolymers are also known.

U.S. Pat. No. 4,693,969 describes a reagent for immunoassays of the sandwich type and a method for its production. The reagent for immunoassays, containing an immunoenzymatic conjugate in polymerized form, enables the sensitivity of the assays of substances present at low concentrations in biological samples, such as hormones, to be increased. This reagent is obtained by synthesizing, in a first stage, antibody-enzyme immunoconjugates in monomer form using a coupling agent (m-maleimidobenzoic acid N-hydroxysuccinimide ester). In a second stage, the monomers are subjected to a polymerization reaction with glutaraldehyde or carbodiimide.

Application EP 430,510 describes a polymer based on "detectable" units joined to one another with a coupling agent. These "detectable" units either have antigenic activity, or form part of a fluorescent, chemoluminescent, chromogenic or enzymatic system. The "detectable" units are joined to one another with a hydrophilic coupling agent which is a 1,4-di(aminoalkyl)piperazine derivative. To obtain these polymers, the "detectable" units are chemically modified so as to contain either two carboxyl groups, or a carboxyl group and an amino or thiocyanate group. The polymerization with the 1,4-di(aminoalkyl)piperazine derivatives is performed employing traditional methods used either in the chemistry of production of peptides from amino acids, or in the chemistry polymer synthesis (use of reagents for condensation of peptides or dialdehydes).

Application EP 175,560 describes a method for obtaining a conjugate consisting of a polymerized enzyme and an antibody. According to this method, a prepolymerized enzyme is obtained in a first stage by covalent coupling of at least two molecules of enzyme via their free thiol or amine groups. This prepolymerized enzyme is then coupled by covalent bonds to an antibody or antibody fragment.

At the present time, it is necessary for some pathologies to detect the presence of an antigen or of a specific antibody at a very early stage. Furthermore, some antigens are sometimes masked from detection, and only minuscule amounts of antibodies specific for the antigen appear in the serum of the patient suffering from such an infection.

The known conjugates of the prior art do not permit a sufficiently sensitive detection of the antigens or antibodies present in the serum of patients suffering from infection which does not induce a substantial immunological reaction.

It is the intention of the present application to provide a solution to this problem of lack of sensitivity by the use of the immunoenzymatic conjugates according to the invention.

The subject of the invention is immunoenzymatic conjugates, which conjugates consist of glycosylated labelling enzymes in copolymer form and substances having immunological activity, and the use of these conjugates in an immunoassay.

The invention also relates to the method for the production of the copolymerized immunoenzymatic conjugates according to the invention, as well as to the use of the said conjugates for immunological determination.

The invention also relates to kits for diagnosis comprising the conjugates according to the invention.

The terms "carbohydrate" or "glycosyl", associated with the enzyme, will be used hereinafter to mean that the enzyme possesses one or more carbohydrate groups lined to its protein portion.

The conjugates according to the invention enable much more sensitive results to be obtained than those obtained with the already known immunoenzymatic conjugates of the prior art. Hence the invention contributes a significant improvement to the field of diagnosis, and especially for the diagnosis of pathologies having a viral origin, since the latter are often difficult to detect, and hence to diagnose, at the beginning of the infection.

The present invention relates more especially to immunoenzymatic conjugate consisting of:

molecules of labelling enzyme copolymerized with one another via their previously oxidized carbohydrate groups, so as to form an enzyme copolymer, and at least one substance having immunological activity, conjugated to the molecules of copolymerized labelling enzyme via free amine groups of the enzyme copolymer.

The conjugates according to the invention consist of labelling enzymes possessing a carbohydrate portion, such as horseradish peroxidase (HRP), alkaline phosphatase (ALP), galactosidase, glucose oxidase and fructose oxidase. Conjugates consisting of copolymers consisting of the said enzymes mentioned, copolymers according to the enzyme chosen, are thereby obtained by the method according to the invention.

According to the invention, the enzyme copolymer is obtained from labelling enzyme and diamine(s), or from labelling enzyme and different heterobifunctional reagents, linked to one another.

According to an advantageous variant, the invention relates to a conjugate in which the enzyme copolymer is obtained from a diamine chosen from an aliphatic diamine (having a linear or branched or cyclic chain) or an aromatic diamine, which amines comprise from 2 to 12 carbon atoms. 1,4-phenylenediamine is preferably used.

According to another advantageous variant, the invention relates to a conjugate in which the enzyme copolymer contains two different heterobifunctional reagents linked to one another, which are chosen, respectively, from 2-mercaptoethylamine or 3-(2-pyridyldithio) propionohydrazide, and 4-(maleimidomethyl)-1-cyclohexanecarbohydrazide or 4-(4-maleimidophenyl) butyrohydrazide.

More specifically, the invention relates to a conjugate in which the enzyme copolymer comprises proportions of enzymes and of diamines or of heterobifunctional reagents of, respectively, 1:1–10 molar equivalents, and preferably 1:4–6 molar equivalents.

Preferably, the invention relates to a conjugate in which the enzyme copolymer comprises n molecules of enzyme, n being an integer between 3 and 100, and preferably an integer between 5 and 50.

According to an advantageous variant, the invention relates to a conjugate in which the copolymerized enzyme is horseradish peroxidase or alkaline phosphatase.

The immunoenzymatic conjugate of the invention is a conjugate in which the enzyme copolymer is coupled to at least one substance having immunological activity via a homo- or heterobifunctional reagent which reacts with an amine function of the enzyme copolymer.

More especially, the invention relates to a conjugate in which the respective molar proportions of the enzyme copolymer and of substance(s) having immunological activity are from 10:1 to 1:10 (enzyme unit/unit of substance having immunological activity), preferably 3:1 to 1:3, and as a further preference 1:1.

Substances having immunological activity, coupled to the enzyme copolymers, can be natural or recombinant proteins, mono- or polyclonal antibodies, recombinant or otherwise, or peptides such as peptides derived from viruses such as HIV (1 or 2), HCV and HBV, recombinant or otherwise.

According to a preferred variant, the invention relates to a conjugate in which the substance having immunological activity is an HIV1 peptide, a HIV2 peptide, an HCV peptide, a recombinant HCV protein, an anti-HIV1 antibody or an anti-HBsAg antibody.

The homo- or heterobifunctional coupling reagents used in the step of coupling of the enzyme copolymer with the substance having immunological activity may be, for example, bis(sulphosuccinimidyl) suberate ($BS^3$), sulpho-succinimidyl 4-(maleimidomethyl)-1-cyclohexanecarboxylate (sulpho-SMCC) or N-succinimidyl 3-(2-pyridyldithio)propionate (SPDP).

The subject of the invention also a method for the production of the conjugate according to the invention, characterized in that:

a. the molecules of labelling enzyme are copolymerized via their previously oxidized carbohydrates, b. coupling of the enzyme copolymer with at least one substance having immunological activity is then performed.

For the oxidation of the enzyme carbohydrate, reagents enabling aldehyde groups to be obtained are used. For example, an oxidation with periodate, or any other equivalent oxidation enabling aldehyde groups to be obtained, is employed.

In a first embodiment, in the copolymerization step of the method for the production of conjugates according to the invention, the molecules of enzyme are reacted with a diamine.

In a second embodiment, in the copolymerization step of the method for the production of conjugates according to the invention, the molecules of enzyme(s) are reacted separately with two different heterobifunctional reagents in a first step, and the products of the reaction are then reacted with one another in a second step.

According to an advantageous variant, the invention relates to a method for the production of a copolymerized immunoenzymatic conjugate in which, after the copolymerization of the molecules of labelling enzyme(s), when a diamine is used, a reduction is performed with a reducing agent such as sodium borohydride or sodium cyanoborohydride, which has the effect of stopping the copolymerization.

According to another advantageous variant, the invention relates to a method for the production of a copolymerized immunoenzymatic conjugate in which, after the copolymerization of molecules of labelling enzyme(s), when different heterobifunctional reagents are used, a reaction is performed with agents that block the unreacted free groups of the heterobifunctional reagents. It is possible, depending on the case, either to use both of the agents that block the free groups of both of the reagents used, or to use one of the two agents that block the free groups of the reagents employed.

Preferably, the invention relates to a method for the production of a copolymerized immunoenzymatic conjugate, according to which, in the step of coupling of the enzyme copolymer with the substances having immunological activity, the concentration of the homo- or heterobifunctional coupling reagent is in excess relative to the concentration of the enzyme copolymer.

The production method according to the invention is described in greater detail below for a copolymerization performed in one step:

The enzyme chosen to perform the production of the conjugate is, prior to the copolymerization reaction, treated with a reagent that oxidizes carbohydrate groups, such as periodate (several hundred mol/mole of enzyme) at a pH of between 4 and 8. The excess periodate is then removed by dialysis of the solution of oxidized enzyme.

An aliphatic (linear, branched or cyclic) or aromatic diamine comprising from 2 to 12 carbon atoms, preferably 1,4-phenylenediamine, is then added at a concentration of 1:1–10 molar equivalents (enzyme unit/diamine unit), and preferably 1:4–6 molar equivalents, in a medium whose pH is between 7 and 9.5.

The copolymerization reaction is monitored by gel filtration chromatographic analysis to obtain enzyme copolymers which comprise n enzyme motifs, n being an integer from 3 to 100, and preferably an integer from 5 to 50.

The copolymerization reaction is then stopped by adding an excess of an agent for reducing the oxidized carbohydrates which have not reacted during the copolymerization reaction, such as sodium borohydride or sodium cyanoborohydride.

The enzyme copolymer thereby obtained is then purified by gel filtration.

The enzyme copolymer is thereafter activated by adding a homo- or heterobifunctional reagent in proportions of 5–50 mol/mole of enzyme, at a pH of between 6.5 and 8. The activated enzyme copolymers are then purified by desalting on gel.

Conjugation of the activated enzyme copolymer with the substance having immunological activity is thereafter performed using molar proportions of approximately 10:1 to 1:10 (enzyme unit/unit of substance having immunological activity), preferably 3:1 to 1:3, and as a further preference 1:1, this reaction being performed at neutral pH.

The production method according to the invention is described in greater detail below for a copolymerization performed in two steps:

The enzyme chosen to perform the production of the conjugate is, prior to the copolymerization reaction, treated with a heterobifunctional reagent that oxidizes carbohydrate groups, such as periodate (several hundred mol/mole of enzyme) at a pH of between 4 and 8. The excess periodate is then removed by dialysis of the solution of oxidized enzyme.

The solution of oxidized enzyme is adjusted to 5–10 mg/ml and divided into 2 equal portions.

A heterobifunctional reagent such as 2-mercaptoethylamine is then added to the first portion at a concentration of 1:1–10 molar equivalents (enzyme unit/diamine unit), and preferably 1:4–6 molar equivalents, in a medium whose pH is between 7 and 9.5, and reaction is carried out for one hour at room temperature.

A reagent such as 4-(maleimidomethyl)-1-cyclohexanecarbohydrazide is added to the second portion at a concentration such as is defined above, and reaction is carried out for one hour at room temperature.

According to a preferred variant, for the step described above, the following protocol is performed:

A reagent such as 3-(2-pyridyldithio)propionohydrazide (PDPH) is added to the first portion at a final concentration of approximately 5 mM, at pH 5–7. The reactants are allowed to react for approximately one hour at 20° C.

A reagent such as 4-(4-maleimidophenyl)butyrohydrazide (MPBH) is added to the second portion at a final concentration of approximately 1 mM, at pH 5–7. The reactants are allowed to react for approximately 1 hour at 20° C.

Each of the enzyme solutions is filtered and purified by gel filtration.

The fraction activated with PDPH is reduced with diethiothreitol (final concentration 10 mM) for approximately 10 minutes, and then purified again by gel filtration.

The enzyme fraction activated with PDPH after reduction is mixed with the enzyme fraction activated with MPBH. The copolymerization reaction of the 2 species is performed at 20° C. at a pH of between 6 and 8.

According to the method of the invention, monitoring of the copolymerization is performed by gel filtration using an analytical column, the exact characteristics of which are chosen in accordance with the enzyme which forms the copolymer. For example, a column packed with Pharmacia Superose® 6 Prep Grade gel is used for alkaline phosphatase (MW=140,000), or with Superose® 12 Prep Grade for horseradish peroxidase (MW=44,000).

According to the method of the invention, at the end of the copolymerization, blocking of the reactions is carried out by successive additions of 2-mercaptoethanol (final concentration 1 mM) and N-ethylmaleimide (final concentration 2 mM). A reduction with sodium borohydride or sodium cyanoborohydride may be performed in order to reduce any carbonyl groups which may not have reacted, and to stabilize the hydrazone groups created by the reaction of the carbonyl groups with the hydrazides.

The solution of polymerized enzyme is purified by gel filtration on a preparative column under conditions similar to the above analytical monitoring. The fraction corresponding to the species excluded from the gel is recovered and constitutes the solution of polymerized enzyme. The protein concentration is determined by BCA assay (Pierce).

The enzyme copolymer is thereafter activated by adding a homo- or heterobifunctional reagent in proportions of 5–50 mol/mole of enzyme, at a pH of between 6.5 and 8. The activated enzyme copolymers are then purified by desalting on gel.

Conjugation of the activated enzyme copolymer with the substance having immunological activity is then performed using molar proportions of approximately 10:1 to 1:10 (enzyme unit/unit of substance having immunological activity), preferably 3:1 to 1:3, and as a further preference 1:1, this reaction being performed at neutral pH.

Depending on the choice of the conjugate it will be preferred to obtain, the free amine groups of the enzymes either will or will not be blocked before the copolymerization reaction.

In so far as the free amine groups of the enzyme molecules are not blocked, it will be preferable to use an aromatic diamine such as, for example, 1,4-phenylenediamine or heterobifunctional reagents during the copolymerization reaction.

In so far as the free amine groups of the enzyme molecules are blocked before the copolymerization reaction with a protective agent for amino groups, the copolymerization reaction may be performed with an aliphatic diamine (linear, branched or cyclic) or an aromatic amine comprising from 2 to 12 carbon atoms, or heterobifunctional reagents.

The copolymerization reaction may then be undertaken and, depending on the point at which it is desired that the coupling of the substance having immunological activity to the enzyme copolymer via homo- or heterobifunctional reagent shall react, the group protecting the amine functions either will or will not be removed.

The coupling of the enzyme copolymer with the substance having immunological activity can take place either on the protein portion of the enzyme copolymer, or on the diamines or heterobifunctional reagents which have previously reacted through one of their ends with the oxidized sugar portions and have not reacted through the other end, or on both at once.

It is apparent from the foregoing description that the method for the production of conjugates according to the invention comprising a one-step copolymerization makes possible, in addition to the obtaining of conjugates displaying a considerable gain in sensitivity in immunoenzymatic tests, advantageous variants of production.

It is also apparent from the foregoing description that the advantage of the method for the production of conjugates according to the invention comprising a two-step copolymerization is a larger range of choice of coupling sites for the substance having immunological activity.

Suitable immunoconjugates, consisting of the copolymer of chosen enzyme and of substance having immunological activity specific to the infection, may hence be obtained by the choice of the method for the production of the conjugates according to the invention in accordance with the infection it is desired to diagnose. The possible combinations of the method for the production of the conjugates according to the invention (whether in respect of the step of copolymerization of one or more different copolymerized enzymes or the step of coupling of one or more substances having immunological activity which are used) are varied and make it possible, by a judicious choice, to obtain conjugates which achieve specific and extremely sensitive detection results.

In the description of the examples which follow, given without implied limitation, the columns of the chromatography system (Superose® 12 Prep Grade gel and HR 10×30 and XK 16×70 columns, PHARMACIA) are rinsed and equilibrated with previously outgassed PBS buffer (50 mM/pH=7.4).

EXAMPLE 1

Peroxidase-HIVI Peptide Conjugate a—One-step copolymerization of peroxidase:

To carry out the copolymerization, the following buffers (Bfr) are prepared:

PBS Bfr (50 mM sodium phosphate, 0.15 M NaCl/pH—7.4) 2.0 l

HEPES Bfr (0.36 M/pH=5.4) 0.1 l

Sodium acetate Bfr (0.01 M/pH=5.4) at least 1000 times the volume of oxidized peroxidase Sodium carbonate Bfr (1 M/pH=9.0) 15% of the volume of peroxidase For the calculations of concentrations and amounts, optical density (OD) readings are performed at 280 and 403 nm; the mass extinction coefficients are:

$\epsilon 280 = 0.7$ ml.mg$^{-1}$.cm$^{-1}$ $\epsilon 403 = 1.93$ ml.mg$^{-1}$.cm$^{-1}$ The molecular weight of peroxidase is 44,000 Da.

Peroxidase (100 mg) is prepared at a theoretical concentration of 45 mg/ml in HEPES buffer, then checked by measuring the OD at λ280 and 403 nm. The concentration should be 35 mg/ml to within 15%. It is then oxidized by adding periodate (1.5 times the amount of peroxidase at a concentration of 100 mg/ml in HEPES buffer). This oxidation lasts 45 minutes plus or minus 10 minutes at approximately 20° C., and is performed with constant stirring.

A dialysis is next carried out, which is performed at 4° C. in three steps corresponding to three volumes of sodium acetate buffer which greatly exceed the volume of oxidized peroxidase. The total dialysis time should be approximately 24 hours.

The copolymerization takes place in an alkaline medium obtained by adding sodium carbonate buffer and in the presence of 4 molar equivalents of 1,4-phenylenediamine at a concentration of 2 mg/ml in sodium carbonate buffer. This step takes place at 20° C. with stirring and for about 12 hours.

Monitoring of the copolymerization is performed by injecting 25 μl of copolymerized peroxidase onto Superose® gel in an HR 10×30 analytical column. The profile should be composed of a preponderant peak corresponding to molecular species excluded from the gel. Another two to three peaks may be present and correspond to different states of copolymerization. The reaction is then blocked.

Stopping of the copolymerization is carried out by reducing the oxidized groups of the peroxidase molecules which have not reacted during the copolymerization. The stopping is done by adding sodium borohydride (5% of the volume of peroxidase) at a concentration of 5 mg/ml in solution in water. The mixture is kept stirring for 30 seconds, followed by 15 to 20 minutes at room temperature without stirring.

The same step is repeated a second time under the same conditions.

The copolymers are purified on Superose® gel in an XK 16×70 preparative column. The maximum injectable amount of peroxidase is 200 mg, the maximum volume is 10 ml. The column should be equilibrated in PBS buffer. The flow rate for the purification is 120 ml/hour.

The fraction corresponding to the molecular species excluded or minimally retained by the gel is collected.

The mass extinction coefficient ($\epsilon$) for the peroxidase copolymer is 1.3 ml.mg$^{-1}$.cm$^{-1}$ at λ403 nm.

b—Coupling:

The following buffers are prepared:

PBS Bfr (50 mM sodium phosphate, 0.15 M NaCl/pH=7.4) 2 l

MBU Bfr:

5 mM 2-morpholinoethanesulphonic acid (MES) 5 mM 5 mM boric acid

2 M urea 2 l

The peptide used is the fragment (584–609) of the gp 41 protein of the HIV1 isolate BRU. This peptide corresponds to peptide 39 disclosed in the Genetic Systems Corporation European patent whose publication number is EP 220,273.

The amount of copolymer to be activated is dependent on the amount of peptide to be coupled: 10 to 20 mg of peroxidase for 1 mg of HIV1 peptide.

The peroxidase copolymer is activated with 35 molar equivalents of BS$^3$ at a concentration of 30 mg/ml in PBS buffer for 45 minutes at 20° C. with constant stirring.

Desalting of the activated enzyme copolymer is carried out on Superose® gel equilibrated in MBU, and its function is to separate the activated peroxidase copolymer from unreacted BS$^3$.

The peroxidase copolymer is recovered on emergence from this desalting and adjusted to a concentration of 6 mg/ml.

For conjunction of the activated peroxidase copolymer and the HIV1 peptide, the mole ratio (peptide/peroxidase) is 1:1. The peptide is in solution at a concentration of 5 mg/ml. The correct amounts of activated peroxidase copolymers and peptides are mixed and left stirring constantly for 2 hours at 20° C.

After two hour of conjugation, the mixture is purified on Superose® gel equilibrated in PBS buffer. The peroxidase copolymer/HIV1 peptide mixture is injected onto the column at a flow rate of 120 ml/hour.

The fraction corresponding to the conjugate is recovered, and the concentration is determined by reading OD at λ403 nm ($\epsilon$=1.3 ml.mg$^{-1}$.cm$^{-1}$).

EXAMPLE 2

Alkaline Phosphatase-HIV1 Peptide Conjugate a—One-step copolymerization of alkaline phosphatase:

The same production protocol as is described in Example 1 is performed, but purified alkaline phosphatase is used in place of peroxidase. The molecular weight of alkaline phosphatase is 140,000 Da. To produce the conjugate of Example 2, the polymerization of alkaline phosphatase is performed from a solution of enzyme at a concentration of 12 mg/ml in triethanolamine buffer (pH=7.6) containing 3 M NaCl, 5 mM $MgCl_2$ and 0.2 mM $ZnCl_2$.

Oxidation is carried out with 400 molar equivalents of sodium periodate per molar equivalent of alkaline phosphatase.

Monitoring of the copolymerization is performed on Superose 6 PG gel (Pharmacia).

The mass extinction coefficient ($\epsilon$) for the alkaline phosphatase copolymer is 1.4 $ml.mg^{-1}.cm^{-1}$ at $\lambda 280$ nm, instead of 1.0 $ml.mg^{-1}.cm^{-1}$ for the unpolymerized phosphatase.

b—Coupling:

Coupling of the peptide to polymerized alkaline phosphatase is carried out according to the method described in Example 1, changing the enzyme copolymer. After the coupling reaction, carried out using 3 mol of peptide per mole of enzyme unit, the conjugate is purified on Superose® 6 PG gel equilibrated in 10 mM Tris buffer, pH 8 containing $MgCl_2$ (1 mM) and $ZnCl_2$ (0.1 mM). The fraction excluded from the gel and which corresponds to the conjugate is recovered. The concentration is determined by reading the optical density at 280 nm ($\epsilon=1.4$ $ml.mg^{-1}.cm^{-1}$).

Use of the Conjugate Prepared (Conjugate B) and Comparison with a Conjugate According to the Prior Art (Conjugate A) Containing Unpolymerized Enzyme For the conjugate A, prepared according to the prior art, the enzyme used is not polymerized. The method of coupling the peptide to the enzyme is identical to the coupling method described in this example.

Principle of the Immunoassay Carried Out in the Access® Apparatus (Sanofi Diagnostics Pasteur)

The detection of antibodies directed against the HIV1 virus is based on the principle of the sandwich type chemoluminescent immunoenzymatic technique. The test is based on the use of a solid phase coated with purified antigens including the HIV1 envelope glycoprotein.

The solid phase consists of paramagnetic microbeads (Estapor®, Prolabo, France) in the proportion of 50 μg in 0.1 ml of diluent.

The substrate used for the enzyme is a dioxetane of the AMPPPD type (Tropix) or equivalent.

The sera studied comprise:

13 samples positive for anti-HIV1 antibodies (seroconversion samples, diluted or otherwise, obtained from BBI, NABI, Serologicals, USA), 44 samples negative for anti-HIV1 antibodies.

To use the conjugate described in this example, the following steps are performed:

A series of tubes labelled A and a series of tubes labelled B are prepared.

The following are distributed per tube:

0.1 ml of suspension of sensitized microbeads 0.1 ml of serum under study

After incubation for 20 minutes at 37° C. and washing (three times), 0.26 ml of conjugate is added:

tubes A: conjugate A tubes B: conjugate B

All the tubes are incubated for 20 minutes at 37° C. and washing (three times) is carried out, 0.2 ml of substrate is then added to each tube, the mixtures are left to incubate for 5 minutes at 37° C., and the light emitted, expressed in ALU (arbitrary light units) is then measured in each of the tubes A and B using the Access® photomultiplier.

Results:

1—Establishment of threshold values:

The mean value $\bar{x}$ of the light emitted (ALU) in all the negative samples of the tubes A is calculated and 10 standard deviations (SD) are added, and the value $\bar{x}A+10$ SD is obtained, which is used as the threshold value of the tubes A.

The mean value $\bar{x}$ of the light emitted (ALU) in all the negative samples of the tubes B is calculated and 10 standard deviations (SD) are added, and the value $\bar{x}B+10$ SD (expressed in ALU) is obtained, which is used as the threshold value of the tubes B.

2—Interpretation of the results:

A sample is declared positive if the value of light emitted is greater than the threshold value which corresponds to it.

A sample is declared negative if the value of light emitted is smaller than the threshold value which corresponds to it.

Table I below gives the values obtained.

TABLE I

|  | Conjugate A | | Conjugate B | |
| --- | --- | --- | --- | --- |
| SERUM | ALU | ALU/ X + 10SD | ALU | ALU/ X + 10SD |
| 521-2/50 | 445617 | 2.91 | 1339800 | 15.16 |
| 516-1/3 | 179289 | 1.17 | 537851 | 6.08 |
| 514-1/1 | 150627 | 0.98 | 466845 | 5.28 |
| BB1-Q4-1/40 | 129214 | 0.84 | 102312 | 1.16 |
| BB1 Q6-1/10 | 513387 | 3.36 | 962563 | 10.89 |
| BB1 Q6-1/100 | 128650 | 0.84 | 144469 | 1.63 |
| BB1 Q6-1/200 | 106540 | 0.70 | 106991 | 1.21 |
| BB1 18 1/1 | 211733 | 1.38 | 428775 | 4.85 |
| NABI 241 C | 88785 | 0.58 | 83407 | 0.94 |
| NABI 241 D1/10 | 206477 | 1.35 | 599059 | 6.78 |
| NABI 241 D 1/50 | 154701 | 1.01 | 380851 | 4.31 |
| NABI 241 D 1/100 | 123333 | 0.81 | 224706 | 2.54 |
| BBI K5 1/10 | 139337 | 0.91 | 181874 | 2.06 |
| $\bar{x}N = 44$ | 86809 | | 45719 | |
| SD | 6614 | | 4268 | |
| $\bar{x}$ + 10SD(=TV)* | 152947 | | 88398 | |

*TV = Threshold Value

It emerges very clearly from the results presented that the conjugate according to the invention (B) enables very significantly increased ALU responses to be obtained relative to those for the conjugate A. In addition, it will be noted that six sera (Nos 514; Q4-1/40; Q6-1/100; Q6-1/200; 241D 1/100; K5 1/10) found negative with the conjugate of the prior art (A) become positive with the conjugate according to the invention (B).

These assays hence show clearly that the invention enables an improved sensitivity to be obtained.

EXAMPLE 3

Peroxidase-HIV1 Monoclonal Antibody Conjugate

The same production protocol as is described in Example 1 is performed, but an anti-HIV1 monoclonal antibody, clone HIV-p25-6, deposited at the ATCC No. HB 9409, is used in place of the HIV1 peptide.

Use of the HIV Conjugate Produced (Conjugate B) and Comparison with a Conjugate Produced According to the Prior Art (Conjugate A)

Reagents:

Conjugate B: copolymerized immunoenzymatic conjugate whose production is described above in this example.

Conjugate A: Antibody HIV-p-25-6-Peroxidase conjugate produced according to the technique of Nakane et al (J. Histochem. Cytochem. 1974, 22, p. 1084–1091).

Solid phase: Microplate sensitized with the monoclonal antibodies HIV-p-25-2 and HIV-p-25-3.

Enzyme substrate: TMB (tetramethylbenzidine)

Samples:
  10 negative sera
  6 positive control samples composed of dilution of HIV virus (V1 to V4) or of recombinant protein (RP1 and RP2)
  1 serum blank: well not containing serum but replaced by 0.2 ml of diluent.

Assay protocol:

Implementation of the technique is based on the following steps:

Each serum under study (0.2 ml of sample diluted to ¾) is distributed in a well of the microplate. After incubation for 30 minutes at 40° C., followed by washes, the peroxidase-labelled conjugate (0.2 ml) is added. After a further incubation for 30 minutes at 40° C. followed by a further series of washes, the presence of the immobilized enzyme on the complexes is visualized by incubation in the presence of substrate (TMB) for 30 minutes at room temperature. After the reaction is stopped with $H_2SO_4$, reading is performed in a spectrophotometer at λ450/620 nm.

Results:

Table II shows the comparative results obtained using the two conjugates A and B.

TABLE II

|      | Conjugate A OD | Conjugate B OD |
| --- | --- | --- |
| V1   | 0.295 | 1.699 |
| V2   | 0.178 | 0.935 |
| V3   | 0.110 | 0.534 |
| V4   | 0.087 | 0.323 |
| PR1  | 0.157 | 0.670 |
| PR2  | 0.101 | 0.304 |
| Blank | 0.035 | 0.029 |
| Neg  | 0.040 | 0.045 |
| SD   | 0.008 | 0.011 |
| No   | 10 | 10 |

Table II shows the increase in sensitivity provided by the use of the conjugate B, since the optical densities of the positive controls are significantly increased, with an identical mean for the negative sera.

EXAMPLE 4

Alkaline Phosphatase-HIV1 Peptide Conjugate a—Two-step copolymerization of alkaline phosphatase:

Alkaline phosphatase in solution (10–20 mg/ml in 30 mM triethanolamine buffer, pH 7.6 containing 3 M NaCl, 1 mM $MgCl_2$ and 0.1 mM $ZnCl_2$) is oxidized with sodium periodate (300 mol/mole of enzyme) for 45 minutes at 20° C.

The excess periodate is then removed by dialysis of the solution of oxidized enzyme against 10 mM sodium acetate buffer, pH 5.5 containing 1 mM $MgCl_2$.

After dialysis, the solution of oxidized enzyme is divided into 2 equal portions.

3-(2-Pyridyldithio)propionohydrazide (PDPH) is added to the first portion at a final concentration of 4 mM, the alkaline phosphatase concentration being adjusted to 10 mg/ml. The reaction lasts for 1 hour with stirring at 20° C.

4-(4-Maleimidophenyl)butyrohydrazide (MPBH) is added to the second portion at a final concentration of 1 mM, the alkaline phosphatase concentration being adjusted to 5 mg/ml. The reaction lasts for 1 hour with stirring at 20° C.

Each of the enzyme solutions is filtered and purified by gel filtration in 50 mM sodium phosphate buffer, pH 7.4 containing 150 mM sodium chloride.

The fraction activated with PDPH is reduced with dithiothreitol (final concentration 10 mM) for 10 minutes and then purified again by gel filtration.

The enzyme fraction activated with PDPH after reduction is mixed with the enzyme fraction activated with MPBH. The copolymerization reaction of the two species is performed at 20° C. with stirring for 2 to 15 hours, depending on the size of the copolymers which it is desired to obtain.

Monitoring of the copolymerization is performed by gel filtration on an analytical column packed with Superose® 6 Prep Grade gel (Pharmacia).

Blocking of the reactions is carried out by successive additions of 2-mercaptoethanol (final concentration 1 mM) and N-ethylmaleimide (final concentration 2 mM). A reduction with sodium borohydride or sodium cyanoborohydride may be performed in order to reduce carbonyl groups which may not have reacted, and to stabilize the hydrazone groups created by the reaction of the carbonyl groups with the hydrazides.

The solution of polymerized enzyme is purified by gel filtration on a preparative column under conditions similar to those of the above analytical monitoring. The fraction corresponding to the species excluded from the gel is recovered and constitutes the solution of polymerized enzyme. The protein concentration is determined by BCA assay (Pierce).

Coupling:

The same protocol as is described in Example 2 is performed.

EXAMPLE 5

Peroxidase-Anti-HBsAG Antibody Conjugate

To produce this conjugate, the peroxidase copolymer described in Example 1 (a—One-step copolymerization of peroxidase) is used.

Coupling:

The peroxidase copolymer (5 mg) is activated with 35 molar equivalents of sulphosuccinimidyl 4-(maleimidomethyl)-1-cyclohexanecarboxylate (sulpho-SMCC) dissolved at a concentration of 30 mg/ml in water. The reaction is performed with stirring at 20° C. for 30 minutes.

Desalting of the activated enzyme copolymer is carried out on Superose® gel equilibrated in PBS buffer, and its function is to separate the activated peroxidase copolymer from unreacted sulpho-SMCC.

In parallel with the activation of the peroxidase, thiolation of the monoclonal antibody (clone 10-144) is carried out in the following manner:

0.4 ml of antibody at a concentration of 15 mg/ml is activated with 8 molar equivalents of N-succinimidyl 3-(2-pyridyldithio)propionate (SPDP-Pharmacia) dissolved in absolute ethanol at a concentration of 10 mg/ml. The reaction lasts for 45 minutes at 20° C. with stirring. Desalting of the activated antibody is carried out on a PD-10 type column (Pharmacia) equilibrated in PBS buffer, and its function is to separate the activated antibody from unreacted SPDP. DTT (dithiothreitol Pierce®) is added to the recovered solution of antibody to achieve a final concentration of 10 mM. The DTT is allowed to react for 5–10 minutes before desalting of the thiolated antibody is carried out in the same manner as before.

For coupling of the peroxidase and the antibody, the two solutions obtained above (3 mg of thiolated antibody and 3 mg of the activated peroxidase copolymer, equivalent to 3.4 enzyme units per molecule of antibody) are mixed at 20° C. for 2 hours with stirring.

The reaction is blocked by successive additions 15 minutes apart of β-mercaptoethanol (final concentration 1 mM) and then of N-ethylmaleimide (final concentration 2 mM).

After 15 minutes, the reaction mixture is purified on a column of Superose 12 PG gel equilibrated in PBS and then eluted with PBS. The fraction corresponds to the conjugate (species excluded from the gel) is recovered, and the concentration is determined by protein assay (BCA kit, Pierce).

Use of the Conjugate Produced (Conjugate B: Antibody 10-144-Polymerized Peroxidase) and Comparison with a Conjugate Produced According to the Prior Art (Conjugate A: Antibody 10-144-Unpolymerized Peroxidase) in Detection of HBs Antigen Principle of the immunoassay carried out:
Reagents:
Conjugate B: prepared above
Conjugate A: Antibody 10-144-Peroxidase conjugate produced according to the technique of Nakane et al. (J. Histochem. Cytochem. 1974, 22, p. 1084–1091)

Solid phase: Microplate sensitized with monoclonal antibody 112 A 26 as may be obtained in the HBs Ag Monolisa kit (Sanofi Diagnostics Pasteur)

Enzyme substrate: TMB (tetramethylbenzidine)
Samples:
194 negative sera
1 negative control (tested in several wells per microplate)
Samples (standards) assaying at: 0.1, 0.2, 0.5, 1.0, 3.0 and 5.0 ng/ml Assay protocol:
Implementation of the technique is based on the following steps:

A series of microplates labelled A and a series of microplates labelled B are prepared.

The following are distributed per well:
50 µl of diluent
50 µl of conjugate
  wells A: conjugate A
  wells B: conjugate B
0.1 ml of serum under study After incubation for 1 h 30 min at 40° C. and washing, 0.2 ml of substrate is added.

All the wells are incubated for 30 minutes at 40° C., 0.1 ml of 1.5 N $H_2SO_4$ is added, and the optical density (OD) at λ450/620 nm is then measured in each of the wells A and B.
Results:

Detection limit (or analytical sensitivity) designated by the abbreviation DL:

The detection limit is determined for each microplate by taking the mean of the optical densities obtained with the negative control, and 0.025 optical density unit is then added. In the microplates A, the detection limit was 0.156 ng/ml on average. Hence, with the conjugate of the prior art, the 0.1 ng/ml standard could not be detected. In the microplates B, the detection limit was 0.046 ng/ml on average. Hence, with the conjugate of the invention, it is very clear that the 0.1 ng/ml standard was perfectly well detected.

It will be noted that, both for the microplates A and for the microplates B, all the negative sera were indeed found to be negative, that is to say below the threshold value corresponding to them.

The different results are shown in Table III below.

TABLE III

| SERUM | SERIES A OD | SERIES B OD |
|---|---|---|
| Negative control | 0.011 | 0.010 |
| Detection limit | 0.036 | 0.035 |
| HBsAg (ng/ml) | | |
| 0.1 | 0.021 | 0.074 |
| 0.2 | 0.048 | 0.131 |
| 0.5 | 0.125 | 0.333 |
| 1 | 0.243 | 0.587 |
| 3 | 0.758 | 1.582 |
| 5 | 1.259 | 2.253 |
| Detection limit | 0.156 ng/ml | 0.046 ng/ml |
| 194 negative | <DL | <DL |

The results in Table III demonstrate that the conjugate according to the invention enabled a significantly increased sensitivity to be obtained without, however, giving rise to false-positive results.

EXAMPLE 6

Enzymoimmunoassay of the Peroxidase-HCV Peptide Conjugate

The detection of antibodies directed against the hepatitis C virus (HCV) is based in the example below on the principle of the sandwich type immunoenzymatic technique. The test is based on the use of a solid phase (microplate) sensitized with a purified antigen of the HCV virus (capsid).

Implementation of the test is based on the following reaction steps:

Each serum under study (0.1 ml of sample diluted to ¾) is distributed in a well of the microplate. The peroxidase-labelled conjugate (0.1 ml) is then added. After incubation for 30 minutes at 40° C., followed by washing, the presence of the immobilized enzyme on the complexes is visualized by incubation in the presence of the substrate (TMB) for 30 minutes. After the reaction is stopped with $H_2SO_4$, reading is performed in a spectrophotometer at λ450/620 nm. The presence or absence of anti-HCV antibodies is determined by comparing, for each sample, the optical density (OD) recorded with that of the calculated threshold value (in this case, mean of the negatives+0.2).

Table IV shows the comparative results obtained using 2 conjugates, A and B, produced under different conditions (coupling of a peptide mimicking a portion of the HCV virus capsid protein).

The conjugates A and B produced are described below:

Conjugate A: the peroxidase is untreated and the peptide is coupled using a bifunctional reagent (PBS). The coupling method is the one described in Example 1 using peroxidase.

Conjugate B: the conjugate is produced according to the method described in Example 1, replacing the HIV peptide by the HCV peptide.

TABLE IV

| Samples | Conjugate A OD | Conjugate B OD |
|---|---|---|
| Negative serum | 0.012 | 0.025 |
| Positive sera | | |
| PHV - 903 - 1 | 0.109 | 1.398 |
| PHV - 903 - 2 | 0.308 | >3.0 |

TABLE IV-continued

| Samples | Conjugate A OD | Conjugate B OD |
|---|---|---|
| PHV - 903 - 3 | 0.300 | >3.0 |
| PHV - 903 - 4 | 0.817 | >3.0 |
| PHV - 903 - 5 | 0.555 | >3.0 |
| PHV - 903 - 6 | 0.448 | >3.0 |

Table IV shows the increase in sensitivity obtained on all the PHV-903-seroconversion samples (Panel from Boston Biomedica Inc.). The first sample detected by the known current tests lies between No. 2 and No. 6, but is never No. 1.

These results confirm the previous results and show the value of the present invention.

EXAMPLE 7

Enzymoimmunoassay Employing a Peroxidase-HIV1 Peptide Conjugate

The detection of antibodies directed against the HIV virus is based in the example below on the principle of the sandwich type immunoenzymatic technique. The test is based on the use of a solid phase prepared with purified antigens including the HIV1 virus envelope glycoprotein.

The sera under study (0.1 ml of sample diluted to ¾) are distributed in the wells of the microplate. After incubation of 30 minutes, the peroxidase-labelled conjugate is added after washing. The presence of the enzyme immobilized on the complexes is visualized by incubation in the presence of the substrate after removal of the conjugate fraction remaining free. After the reaction is stopped, reading is performed in a spectrophotometer at 450/620 nm. The presence or absence of anti-HIV1 antibodies is determined by comparing, for each sample, the optical density recorded with that of the calculated threshold value (in this case, mean of the negatives+0.1).

Table IV shows the comparative results obtained using five conjugates produced under different conditions (coupling of a peptide mimicking the immunodominant epitope of the HIV1 virus envelope glycoprotein/amino acids 584–609, isolate BRU, to peroxidase).

The different conjugates produced are described below:

Conjugate A: The peroxidase is untreated and the peptide is coupled using a bifunctional reagent (the coupling method is that of Example 1).

Conjugate B: The peptide is coupled to peroxidase according to the method Nakane et al. (J. Histochem. Cytochem, 1974, 22, 1084–1091) modified in the following manner: 28 mg of peroxidase are oxidized with 19.7 mg of sodium periodate for 1 hour 30 minutes. 1 mg of the peptide is brought into contact with 4 mg of oxidized peroxidase for 3 hours. This protocol does not modify the coupling as such according to the Nakane method.

Conjugate C: The peroxidase is prepared according to the method described in the patent application published under the number EP 601,318, and coupled to the peptide using a bifunctional reagent according to the method described in the method of the said application.

Conjugate D: The conjugate is produced according to the method described in Example 1, using 1,6 hexanediamine as bifunctional copolymerization reagent.

Conjugate E: The conjugate is produced according to the method described in Example 1.

In the tables which follow, the results given are optical density values read on performing enzymoimmunoassays according to the protocol described and using the conjugates A, B, C, D and E described.

The sera used are samples of the panels K, U and Q supplied by Boston Biomedica Inc., as well as 31 sera from normal donor patients negative for the detection of HIV antibodies.

| Panel K | A OD | B OD | C OD | D OD | E OD |
|---|---|---|---|---|---|
| K1 | 0.047 | 0.053 | 0.062 | 0.046 | 0.122 |
| K2 | 0.095 | 0.161 | 0.106 | 0.835 | 1.651 |
| K3 | 0.195 | 0.310 | 0.161 | 2.106 | 3 |
| K4 | 0.243 | 0.463 | 0.399 | 2.816 | 3 |
| Panel U | | | | | |
| U1 | 0.045 | 0.112 | 0.298 | 2.407 | 3 |
| U2 | 0.226 | 1.687 | 3 | 3 | 3 |
| Panel Q | | | | | |
| Q3 | 0.050 | 0.044 | 0.049 | 0.055 | 0.125 |
| Q4 | 0.066 | 0.368 | 1.052 | 2.816 | 3 |
| Q5 | 0.125 | 0.404 | 1.064 | 2.906 | 3 |
| Q6 | 0.116 | 0.382 | 1.009 | 2.836 | 3 |
| Q6 ½ | 0.100 | 0.241 | 0.743 | 2.191 | 3 |
| Q6 ¼ | 0.073 | 0.208 | 0.569 | 2.133 | 3 |
| Q6 ⅛ | 0.055 | 0.135 | 0.356 | 1.523 | 2.837 |
| Q6 1/16 | 0.047 | 0.092 | 0.218 | 0.965 | 1.945 |
| Q6 1/32 | 0.047 | 0.081 | 0.163 | 0.668 | 1.515 |
| Q6 1/64 | 0.042 | 0.064 | 0.118 | 0.430 | 0.772 |
| mean (n = 31) | 0.039 | 0.047 | 0.040 | 0.031 | 0.037 |
| threshold value (tv) | 0.139 | 0.147 | 0.140 | 0.131 | 0.137 |

The results of the tests collated in the tables show that only the conjugates D and E enable the positive response both of the sera K2 and Q6 diluted to 1/64 to e detected.

Hence it is apparent that the conjugates according to the invention enable a better detection sensitivity to be obtained than the known conjugates of the prior art. The detection of antibodies directed against HIV1 virus proteins is thus earlier.

We claim:

1. A method for detecting the presence of an antigen or antibody of interest in a biological sample, comprising the steps of:

contacting said biological sample with an immunoenzymatic conjugate of glycosylated labeling enzymes and substances having immunological activity, consisting of:

molecules of labeling enzyme copolymerized with one another via their previously oxidized carbohydrate groups, so as to form an enzyme copolymer, and at least one substance having immunological activity, conjugated to the molecules of copolymerized labeling enzyme via free amine groups of the enzyme copolymer;

said substance having immunological activity being capable to specifically bind to said antigen or antibody present in the biological sample;

detecting the presence of a complex formed between said antigen or antibody and said immunoenzymatic conjugate.

2. A method according to claim 1, wherein the enzyme copolymer is obtained from labeling enzyme and diamine (s), or from labeling enzyme and different heterobifunctional reagents, linked to one another.

3. A method according to claim 1, wherein the diamine is chosen from a diamine comprising 2 to 12 carbon atoms, which is an aliphatic diamine having a linear or branched or cyclic chain or an aromatic diamine.

4. A method according to claim 1, wherein the diamine is 1,4-phenylenediamine.

5. A method according to claim 1, wherein the different heterobifunctional reagents are two heterobifunctional reagents chosen, respectively, from 2-mercaptoethylamine or 3-(2-pyridylthio)propionohydrazide, and 4-(maleimidomethyl)-1-cyclohexanecarbohydrazide or 4-(4-maleimidophenyl)butyrohydrazide.

6. A method according to claim 1, wherein the proportions of enzyme and of diamine or heterobifunctional reagents, are respectively, 1:1–10 molar equivalents, and preferably 1:4–6 molar equivalents.

7. A method according to claim 1, wherein the enzyme copolymer comprises n molecules of enzyme, n being an integer between 3 and 100, and preferably an integer from 5 to 50.

8. A method according to claim 1, wherein the copolymerized enzyme is horseradish peroxidase or alkaline phosphatase.

9. A method according to claim 1, wherein the enzyme copolymer is coupled to at least one substance having immunological activity via a homo- or heterobifunctional reagent.

10. A method according to claim 1, wherein the respective molar proportions of the enzyme copolymer and of the substance having immunological activity are from 10:1 to 1:10 (enzyme unit/unit of substance having immunological activity), preferably 3:1 to 1:3, and as a further preference 1:1.

11. A method according to claim 1, wherein the substance having immunological activity is an HIV1 peptide, an HIV2 peptide, an HCV peptide or an anti-HIV1 monoclonal antibody or an anti-HbsAg antibody.

12. An immunoenzymatic conjugate of glycosylated labelling enzymes and substances having immunological activity, consisting of:

molecules of labelling enzyme copolymerized with one another via their previously oxidized carbohydrate groups, so as to form an enzyme copolymer, and at least one substance having immunological activity, conjugated to the molecules of copolymerized labelling enzyme via free amine groups of the enzyme copolymer.

13. A conjugate according to claim 12, wherein the enzyme copolymer is obtained from labelling enzyme and diamine(s), or from labelling enzyme and different heterobifunctional reagents, linked to one another.

14. A conjugate according to claim 13, wherein the diamine is chosen from a diamine comprising 2 to 12 carbon atoms, which is an aliphatic diamine having a linear or branched or cyclic chain or an aromatic diamine.

15. A conjugate according to claim 13, wherein the diamine is 1,4-phenylenediamine.

16. A conjugate according to claim 13, wherein the different heterobifunctional reagents are two heterobifunctional reagents chosen, respectively, from 2-mercaptoethylamine or 3-(2-pyridyldithio)propionohydrazide, and 4-(maleimidomethyl)-1-cyclohexanecarbohydrazide, or 4-(4-maleimidophenyl)butyrohydrazide.

17. A conjugate according to claim 13, wherein the proportions of enzyme and of diamine or of heterobifunctional reagents are, respectively, 1:1–10 molar equivalents, and preferably 1:4–6 molar equivalents.

18. A conjugate according to claim 12, wherein the enzyme copolymer comprises n molecules of enzyme, n being an integer between 3 and 100, and preferably an integer from 5 to 50.

19. A conjugate according to claim 12, wherein the copolymerized enzyme is horseradish peroxidase or alkaline phosphatase.

20. A conjugate according to claim 12, wherein the enzyme copolymer is coupled to at least one substance having immunological activity via a homo- or heterobifunctional reagent.

21. A conjugate according to claim 12, wherein the respective molar proportions of the enzyme copolymer and of the substance having immunological activity are from 10:1 to 1:10 (enzyme unit/unit of substance having immunological activity), preferably 3:1 to 1:3, and as a further preference 1:1.

22. A conjugate according to claim 12, wherein the substance having immunological activity is an HIV1 peptide, a HIV2 peptide, an HCV peptide or an anti-HIV1 monoclonal antibody or an anti-HBsAg antibody.

23. A method for the production of conjugate according to claim 12, wherein:

a. the molecules of labelling enzyme are copolymerized via their previously oxidized carbohydrates, b. a coupling of the enzyme copolymer with at least one substance having immunological activity is then performed.

24. A method according to claim 23, in which, to perform the copolymerization, the molecules of enzyme are reacted with a diamine.

25. A method according to claim 23, in which, to perform the copolymerization, the molecules of enzyme are reacted separately with two different heterobifunctional reagents in a first step, and the reaction products are then reacted with one another in a second step.

26. A method according to claim 23, wherein, after the copolymerization, a reduction is performed with a reducing agent chosen from sodium borohydride and sodium cyanoborohydride.

27. A method according to claim 23, wherein, after the copolymerization, a reaction is performed with agents that block the heterobifunctional reagents.

28. A method according to claim 23, wherein, in the step of coupling of the enzyme copolymer with the substance or substances having immunological activity, the concentration of the homo- or heterobifunctional reagent is in excess relative to the concentration of the enzyme copolymer.

29. A diagnostic kit for immunological determination, comprising an immunoenzymatic conjugate according to claim 12.

* * * * *